US00PP10164P

United States Patent [19]

Olesen et al.

[11] Patent Number: Plant 10,164

[45] Date of Patent: Dec. 30, 1997

[54] MINIATURE ROSE PLANT NAMED 'POULTIN'

[75] Inventors: Mogens N. Olesen; Pernille Olesen, both of Fredensborg, Denmark

[73] Assignee: Bear Creek Gardens, Inc., Medford, Oreg.

[21] Appl. No.: 606,893

[22] Filed: Feb. 21, 1996

[51] Int. Cl.[6] ..... A01H 5/00

[52] U.S. Cl. ..... Plt./9

[58] Field of Search ..... Plt./7.1, 9, 10

*Primary Examiner*—Howard J. Locker

*Attorney, Agent, or Firm*—Klarquist Sparkman Campbell Leigh & Whinston, LLP

[57] ABSTRACT

A miniature rose plant having a compact, vigorous and even growth habit, dark green, glossy foliage, bright pink flowers, long shelf life, and being readily propagated by softwood cuttings.

1 Drawing Sheet

1

The present invention relates to a new and distinct variety of rose plant of the miniature class which was originated by us by crossing the variety MEIbinosor, unpatented, with the variety RUImissa, U.S. Plant Pat. No. 7,051.

The primary objective of this breeding was to produce a new rose variety having the vigorous bushy growth and healthy foliage of the female parent combined with the compact miniature growth and abundance of flowers of the male parent. The objective was substantially achieved, along with other desirable improvements, as evidenced by the following unique combination of characteristics that are outstanding in the new variety and that distinguish it from its parents, as well as from all other varieties of which we are aware:

1. Dark green, glossy foliage;
2. Compact, vigorous growth;
3. Bright pink, well formed flowers;
4. Ease of rooting from softwood cuttings; and
5. Long shelf life in bloom.

Asexual reproduction of this new variety by softwood cuttings, as performed at Wasco and Somis, Calif., and Fredensborg, Denmark, shows that the foregoing and all other characteristics and distinctions come true to form and are established and transmitted through succeeding propagation.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—MEIbinosor.

*Pollen parent.*—RUImissa.

Classification:

*Botanical.*—Rosa hybrida.

*Commercial.*—Miniature.

FLOWER

Observations made from specimens grown in a greenhouse environment at Somis, Calif., and Fredensborg, Denmark.

2

Blooming habit: Continuous.

Bud:

*Size.*—¾ inch long when the petals start to unfurl.

*Form.*—The bud form is short, pointed ovoid.

*Color.*—When sepals first divide, bud color is Red Purple Group 62B. When half blown, the upper sides of the petals are Red Purple Group 58B; and the lower sides of the petals are Red Purple Group 62B.

*Sepals.*—Color: Green Group 137D. Surface texture: Covered in fine hairs. There are three lightly appendaged sepals. There are two unappendaged sepals with hairy edges and a few glands.

*Receptacle.*—Color: Green Group 137D. Shape: Funnel. Size: Small (3/16"×1/8"). Surface: Smooth with a few fine hairs.

*Peduncle.*—Length: Short (1–1¼". Surface: Glandular. Color: Medium green. Strength: Stiff and erect.

Bloom:

*Size.*—Small. Average open size is 1¾–2".

*Borne.*—Singly.

*Stems.*—Short and strong. Average length is about 6–8 inches.

*Form.*—When first open: High center. Permanence: Flattens, outer petals curl back.

*Petalage.*—Number of petals under normal conditions: 20–25.

*Color.*—The upper sides of the petals are Red-Purple Group 58B; their outer margins being Red-Purple Group 58D. The reverse sides of the petals are Red Purple Group 62B. The base of each petal has a small half moon at the point of attachment that is Yellow Group 2B The major color on the upper side is Red Purple Group 58B.

*Variegations.*—None.

*Discoloration.*—There are no change in tonality of the petals until the petals drop on day 6 or 7.

*Fragrance.*—Slight.

*Shelf life.*—Under low light, urban conditions plant will have twelve or more days of continuous bloom.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Long (6–7 days). As a cut flower: Not tested.

Reproductive Parts:

*Anthers.*—Size: Medium. Quantity: Many. Color: Reddish brown. Arrangement: Regular around styles.

*Filaments.*—Color: Yellow.

*Pollen.*—Color: Gold yellow.

*Styles.*—Color: Greenish white.

*Stigmas.*—Color: Greenish white.

Form: Bush.

Growth: Vigorous, dwarf, upright, branching, and compact. Height in a 5-inch pot at full flower is about 10 inches.

Foliage: Number of leaflets on normal mid-stem leaves: 5.

*Size.*—Small (3"×2").

*Quantity.*—Abundant.

*Color.*—New foliage: Some anthocyanin on leaf margins of Greyed-Red Group 178B which changes rapidly to a green coloration. Upper: Yellow Green 146B. Lower: Yellow Green 147C. Old foliage: Upper: Green Group 139A. Lower: Green Group 139C.

Leaflets:

*Shape.*—Pointed oval.

*Texture.*—Upper side: Glossy and smooth.

*Edge.*—Serrated.

*Serration.*—Single and small.

*Petiole rachis.*—Color: Green.

*Petiole underside.*—Smooth, with a few small prickles.

*Stipules.*—Short (3/16"), serrated, and bearded.

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short (1/8") and straight.

*Color when young.*—Red.

Small prickles:

*Quantity.*—On main stalks: None. On laterals: None.

We claim:

1. A new and distinct variety of rose plant of the miniature class, substantially as herein shown and described, characterized particularly as to novelty by the combination of dark green glossy foliage; long shelf life; ease of propagation by softwood cuttings; attractive bright pink flowers; and vigorous compact growth.

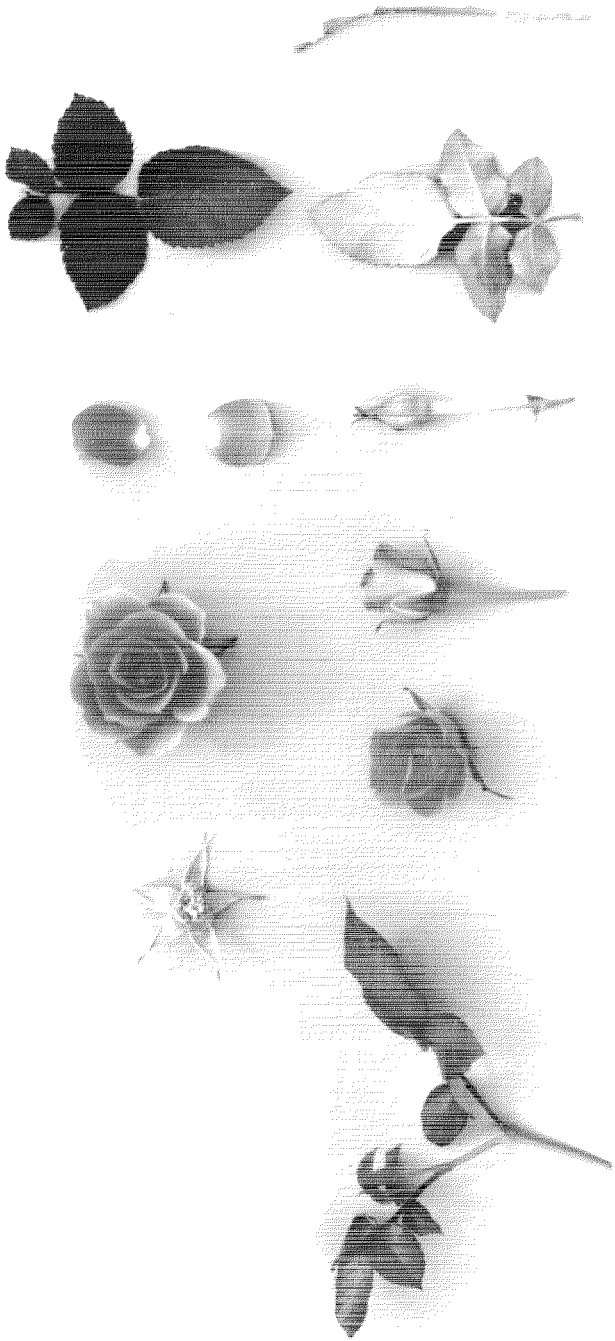

* * * * *